United States Patent
Nakamura (10) Patent No.: US 11,280,776 B2
(45) Date of Patent: *Mar. 22, 2022

(54) CONCENTRATION MEASUREMENT METHOD AND CONCENTRATION MEASUREMENT DEVICE

(71) Applicant: HAMAMATSU PHOTONICS K.K., Hamamatsu (JP)

(72) Inventor: Tomonori Nakamura, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/969,214

(22) PCT Filed: Jan. 17, 2019

(86) PCT No.: PCT/JP2019/001345
§ 371 (c)(1),
(2) Date: Aug. 12, 2020

(87) PCT Pub. No.: WO2019/159597
PCT Pub. Date: Aug. 22, 2019

(65) Prior Publication Data
US 2020/0408730 A1    Dec. 31, 2020

(30) Foreign Application Priority Data

Feb. 16, 2018   (JP) .............................. JP2018-025797

(51) Int. Cl.
*G01N 33/00*   (2006.01)
*G01N 21/41*   (2006.01)
*G02B 27/30*   (2006.01)

(52) U.S. Cl.
CPC ......... *G01N 33/0067* (2013.01); *G01N 21/41* (2013.01); *G01N 2021/418* (2013.01); *G02B 27/30* (2013.01)

(58) Field of Classification Search
CPC ............... G01N 21/3581; G01N 21/41; G01N 33/0067; G01N 2021/418; G02B 27/30
See application file for complete search history.

(56) References Cited

U.S. PATENT DOCUMENTS

| 4,952,063 A | * | 8/1990 | Opsal | ................... G01N 21/171 356/432 |
| 2004/0196464 A1 | * | 10/2004 | Akutsu | .............. G01N 21/1717 356/432 |

(Continued)

FOREIGN PATENT DOCUMENTS

| JP | 2004-311580 A | 11/2004 |
| JP | 2009-521796 A | 6/2009 |

(Continued)

OTHER PUBLICATIONS

International Preliminary Report on Patentability dated Aug. 27, 2020 for PCT/JP2019/001345.

*Primary Examiner* — Sang H Nguyen
(74) *Attorney, Agent, or Firm* — Faegre Drinker Biddle & Reath LLP (57) ABSTRACT

A concentration measurement method for measuring a concentration of impurities includes a step of irradiating a DUT 10 serving as a measurement target object with measurement light and stimulus light subjected to intensity modulation using a modulation signal including a default frequency, a step of outputting a detection signal by detecting an intensity of reflected light from the DUT 10 or transmitted light through the DUT 10, and a step of detecting a phase delay of the detection signal with respect to the modulation signal, obtaining a frequency at which the phase delay has a predetermined value, and estimating a concentration of impurities in the measurement target object on the basis of the frequency.

16 Claims, 6 Drawing Sheets

(56) References Cited

U.S. PATENT DOCUMENTS

| | | | | |
|---|---|---|---|---|
| 2004/0253751 | A1* | 12/2004 | Salnik | G01R 31/2621 |
| | | | | 438/16 |
| 2005/0010092 | A1* | 1/2005 | Weber | A61B 5/7214 |
| | | | | 600/322 |
| 2005/0062971 | A1* | 3/2005 | Salnik | G01N 21/636 |
| | | | | 356/432 |
| 2005/0134857 | A1* | 6/2005 | Maury | G01N 21/1717 |
| | | | | 356/432 |
| 2006/0040308 | A1* | 2/2006 | Capaldi | C07H 21/04 |
| | | | | 435/6.12 |
| 2006/0094133 | A1* | 5/2006 | Takeuchi | G01N 21/1717 |
| | | | | 438/14 |
| 2008/0304047 | A1* | 12/2008 | Lee | G01J 3/433 |
| | | | | 356/51 |
| 2011/0118571 | A1* | 5/2011 | Mandelis | A61B 5/7228 |
| | | | | 600/316 |
| 2012/0310062 | A1* | 12/2012 | Li | A61B 5/14551 |
| | | | | 600/328 |
| 2013/0015368 | A1* | 1/2013 | Nakanishi | G01N 21/9501 |
| | | | | 250/459.1 |
| 2013/0286379 | A1* | 10/2013 | Li | G01N 21/1702 |
| | | | | 356/40 |
| 2018/0284015 | A1* | 10/2018 | Imade | G01N 21/27 |

FOREIGN PATENT DOCUMENTS

| | | |
|---|---|---|
| JP | 2016-157780 A | 9/2016 |
| RU | 2444085 C1 | 2/2012 |
| WO | WO-2007/050570 A2 | 5/2007 |
| WO | WO 2013/016469 A1 | 1/2013 |

* cited by examiner

CONCENTRATION MEASUREMENT METHOD AND CONCENTRATION MEASUREMENT DEVICE

TECHNICAL FIELD

The present disclosure relates to a concentration measurement method and a concentration measurement device for measuring a concentration of impurities in a measurement target object.

BACKGROUND ART

In the related art, a device for performing characteristic evaluation of a measurement target object such as a solar battery is known (for example, refer to the following Patent Literature 1). This device is configured to have a pumping light source irradiating a measurement target object with pulsed pumping light, a probe light source continuously irradiating the measurement target object with probe light, a photo detector detecting the probe light used for irradiating the measurement target object in real time, and a signal processing unit processing a signal output from the photo detector. According to such a configuration, it is possible to measure circumstances of generation and extinction of carriers by measuring a change in carrier quantity over time.

CITATION LIST

Patent Literature

[Patent Literature 1] Japanese Unexamined Patent Publication No. 2016-157780

SUMMARY OF INVENTION

Technical Problem

In such devices in the related art described above, although a change in carrier quantity over time can be measured, it is difficult to measure an exact concentration of impurities targeting a measurement target object whose concentration of impurities is unknown.

An embodiment aims to provide a concentration measurement method and a concentration measurement device capable of accurately measuring a concentration of impurities in a measurement target object.

Solution to Problem

According to an aspect of the present invention, there is provided a concentration measurement method for measuring a concentration of impurities in a measurement target object. The concentration measurement method includes an irradiation step of irradiating the measurement target object with measurement light and stimulus light subjected to intensity modulation using a modulation signal including a default frequency, an outputting step of outputting a detection signal by detecting an intensity of reflected light from the measurement target object or transmitted light through the measurement target object, and an estimation step of detecting a phase delay of the detection signal with respect to the modulation signal, obtaining a frequency at which the phase delay has a predetermined value, and estimating a concentration of impurities in the measurement target object on the basis of the frequency.

Alternatively, according to another aspect of the present invention, there is provided a concentration measurement device for measuring a concentration of impurities in a measurement target object. The concentration measurement device includes a first light source configured to generate measurement light, a second light source configured to generate stimulus light, a modulation unit configured to perform intensity modulation of the stimulus light using a modulation signal including a default frequency, a photo detector configured to output a detection signal by detecting an intensity of reflected light from the measurement target object or transmitted light through the measurement target object, an optical system configured to guide the measurement light and the stimulus light subjected to intensity modulation toward the measurement target object and to guide reflected light from the measurement target object or transmitted light through the measurement target object toward the photo detector, and an analysis unit configured to detect a phase delay of the detection signal with respect to the modulation signal, to obtain a frequency at which the phase delay has a predetermined value, and to estimate a concentration of impurities in the measurement target object on the basis of the frequency.

According to any of the foregoing aspects, a measurement target object is irradiated with measurement light and stimulus light subjected to intensity modulation using a modulation signal including a default frequency, and an intensity of reflected light from the measurement target object or transmitted light through the measurement target object is detected. As a result, a concentration of impurities in the measurement target object is estimated on the basis of an output detection signal. At this time, a frequency at which a phase delay has a predetermined value is estimated on the basis of the phase delay of the detection signal with respect to the modulation signal, and the concentration of impurities is estimated on the basis of the estimated frequency. Therefore, even when a concentration of impurities is unknown, it is possible to accurately measure the concentration of impurities associated with a lifetime of carriers.

Advantageous Effects of Invention

According to an embodiment, it is possible to accurately measure a concentration of impurities in a measurement target object.

DESCRIPTION OF EMBODIMENT

Hereinafter, an embodiment of the present invention will be described in detail with reference to the accompanying drawings. In the description, the same reference signs are applied to the same elements or elements having the same function, and duplicate description will be omitted.

Figure 1:
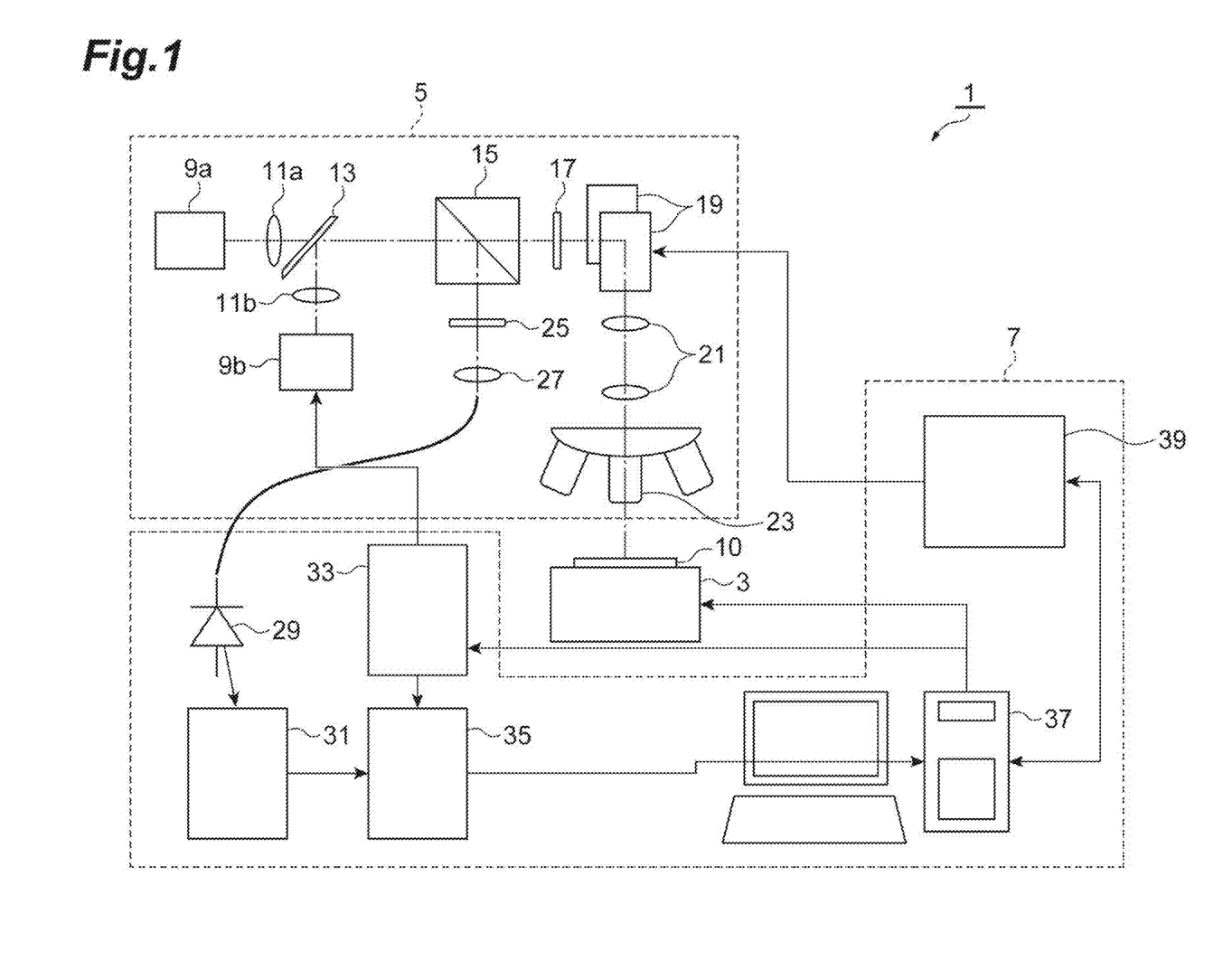
FIG. 1 is a view of a schematic configuration of a concentration measurement device 1 according to an embodiment.

FIG. 1 is a view of a schematic configuration of a concentration measurement device 1 according to the embodiment. The concentration measurement device 1 shown in FIG. 1 is a device for measuring a concentration of impurities or the like in a device under test (DUT) 10 serving as a measurement target object such as a semiconductor device by performing optical measurement targeting the DUT 10. Examples of a measurement target of the concentration measurement device 1 include a bare wafer; a substrate subjected to epitaxial growth at a uniform doping density; a wafer substrate on which a well, a diffusion region, or the like is formed; and a semiconductor substrate on which a circuit element such as a transistor is formed.

This concentration measurement device 1 is configured to include a stage 3 on which the DUT 10 is disposed; a light irradiation/light guiding system (optical system) 5 which guides light toward the DUT 10, irradiates the DUT 10 with the light, and guides reflected light from the DUT 10; and a control system 7 which controls the light irradiation/light guiding system 5, detects reflected light from the DUT 10, and performs processing of the reflected light. The stage 3 is a support unit supporting the DUT 10 so that the DUT 10 faces the light irradiation/light guiding system 5. The stage 3 may be equipped with a movement mechanism which can move the DUT 10 relatively to the light irradiation/light guiding system 5. In FIG. 1, a traveling path of light is indicated by a dashed-dotted line, and a transmission path of a control signal and transmission paths of a detection signal and processing data are indicated by solid arrows.

The light irradiation/light guiding system 5 includes a light source (first light source) 9a, a light source (second light source) 9b, collimators 11a and 11b, a dichroic mirror 13, a polarization beam splitter 15, a quarter-wavelength plate 17, a galvanometer mirror 19, a pupil projection lens 21, an object lens 23, an optical filter 25, and a collimator 27.

The light source 9a generates and emits light as measurement light (probe light) that has a wavelength and an intensity suitable for detecting optical characteristics which change in association with the concentration in the DUT 10. The light source 9b generates and emits light as stimulus light (pumping light) that includes a wavelength component which is partially absorbed in the DUT 10. Specifically, the light source 9b is set to generate stimulus light including a wavelength associated with an energy higher than a bandgap energy of a semiconductor which is a material for a substrate configuring the DUT 10. Moreover, this light source 9b is configured to be able to generate stimulus light subjected to intensity modulation on the basis of an electrical signal from the outside. For example, the light source 9a and the light source 9b may be coherent light sources such as semiconductor lasers or may be incoherent light sources such as super luminescent diodes (SLDs).

The collimators 11a and 11b respectively collimate rays of light emitted from the light sources 9a and 9b, and the dichroic mirror 13 coaxially synthesizes measurement light and stimulus light which have been collimated and outputs the coaxially synthesized light toward the polarization beam splitter 15. The polarization beam splitter 15 allows linearly polarized components of measurement light and stimulus light which have been synthesized to be transmitted therethrough, and the quarter-wavelength plate 17 changes polarization states of the measurement light and the stimulus light which have been transmitted through the polarization beam splitter 15 and sets the polarization states of the measurement light and the stimulus light in circular polarization. The galvanometer mirror 19 performs scanning with measurement light and stimulus light in circular polarization and outputs the measurement light and the stimulus light, and the pupil projection lens 21 relays pupils of measurement light and stimulus light output from the galvanometer mirror 19 to a pupil of the object lens 23 from the galvanometer mirror 19. The object lens 23 collects measurement light and stimulus light on the DUT 10. According to such a configuration, a desired position on the DUT 10 can be scanned and irradiated with measurement light and stimulus light which have been synthesized. In addition, the concentration measurement device 1 may be configured to be able to perform scanning with measurement light and stimulus light targeting a range which the galvanometer mirror 19 cannot cover by moving the stage 3.

In addition, in the light irradiation/light guiding system 5 having the foregoing configuration, reflected light from the DUT 10 can be guided to the quarter-wavelength plate 17 in a manner of being coaxial with measurement light and stimulus light, and the polarization state of reflected light can be changed from circular polarization to linear polarization by the quarter-wavelength plate 17. Moreover, linearly polarized reflected light is reflected toward the optical filter 25 and the collimator 27 by the polarization beam splitter 15. The optical filter 25 is configured to allow only the same wavelength component as that of measurement light of reflected light to be transmitted therethrough toward the collimator 27 and to block the same wavelength component as that of stimulus light of reflected light. The collimator 27 collimates reflected light and outputs the reflected light toward the control system 7 via an optical fiber or the like.

The control system 7 includes a photo detector 29, an amplifier 31, a modulation signal source (modulation unit) 33, a network analyzer 35 (analysis unit), a controller (analysis unit) 37, and a laser scanning controller 39.

The photo detector 29 is a photo detection element such as a photodiode (PD), an avalanche photodiode (APD), or a photomultiplier tube, which receives reflected light guided by the light irradiation/light guiding system 5, detects the intensity of the reflected light, and outputs a detection signal. The amplifier 31 amplifies a detection signal output from the photo detector 29 and outputs an amplified result to the network analyzer 35. The modulation signal source 33 generates an electrical signal (modulation signal) having a waveform set by the controller 37 and controls the light source 9b so that stimulus light is subjected to intensity modulation on the basis of the electrical signal. Specifically, the modulation signal source 33 generates an electrical signal having rectangular waves of a set repetition frequency (default frequency) and controls the light source 9b on the basis of the electrical signal. In addition, the modulation signal source 33 also has a function of repetitively generating an electrical signal having rectangular waves of a plurality of repetition frequencies.

The network analyzer 35 extracts and detects a detection signal having a wavelength component associated with the repetition frequency on the basis of a detection signal output from the amplifier 31 and the repetition frequency set by the modulation signal source 33. Specifically, the network analyzer 35 extracts a detection signal having the same frequency as the repetition frequency and a detection signal having a frequency of higher harmonic waves thereof. Moreover, the network analyzer 35 detects a phase delay of a detection signal having each of the frequencies with respect to stimulus light subjected to intensity modulation on the basis of an electrical signal generated by the modulation signal source 33. Further, the network analyzer 35 inputs information of each of the frequencies of the extracted detection signals and information of a detected phase delay targeting the detection signal to the controller 37 in an associated manner. At this time, the network analyzer 35 may repetitively extract a detection signal targeting an electrical signal having a plurality of repetition frequencies which have been repetitively set by the controller 37 and may detect a phase delay targeting the detection signal. For example, a phase delay may be detected by changing the repetition frequency from a fundamental frequency to frequencies of $1/10$ times, ten times, and the like. Here, the network analyzer 35 may be changed to a spectrum analyzer, may be changed to a lock-in amplifier, or may be changed to a configuration in which a digitizer and an FFT analyzer are combined.

Figure 2:
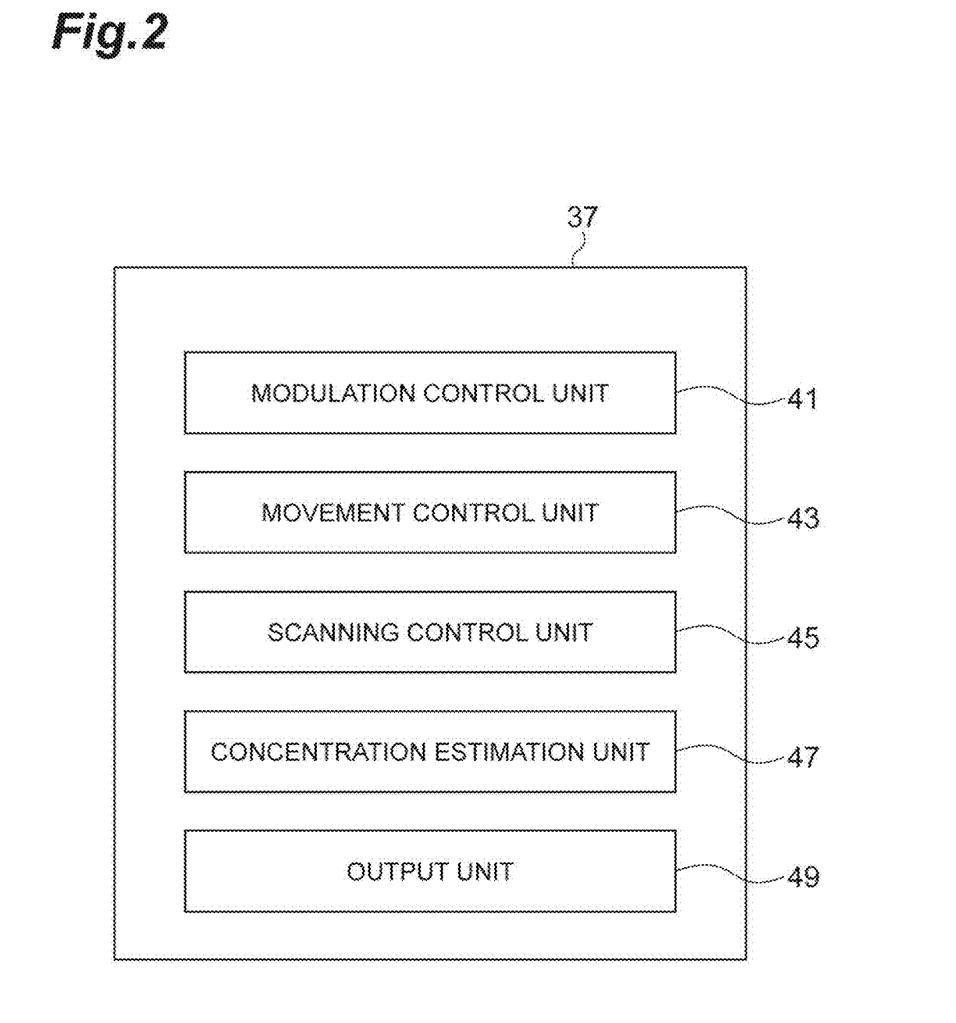
FIG. 2 is a block diagram showing a configuration of functions of a controller 37 in FIG. 1.

The controller 37 is a device for generally controlling operation of the control system 7 and is physically a control device such as a computer including a central processing unit (CPU) serving as a processor, a random access memory (RAM) and a read only memory (ROM) serving as recording mediums, a communication module, and input/output devices such as a display, a mouse, a keyboard, and the like. FIG. 2 shows a configuration of functions of the controller 37. As shown in FIG. 2, as functional constituent elements, the controller 37 is configured to include a modulation control unit 41, a movement control unit 43, a scanning control unit 45, a concentration estimation unit 47, and an output unit 49.

The modulation control unit 41 of the controller 37 sets a waveform of an electrical signal for performing intensity modulation of stimulus light. Specifically, the modulation control unit 41 sets a waveform of an electrical signal to have rectangular waves of a predetermined repetition frequency. This "predetermined repetition frequency" may be a frequency having a value stored in the controller 37 in advance in accordance with a concentration of impurities or the like in a postulated DUT 10 or may be a frequency having a value input from the outside via the input/output device. In addition, the modulation control unit 41 may repetitively change the repetition frequency from a fundamental frequency which has been recorded or input in advance to a plurality of frequencies and may be able to set an electrical signal in accordance with the changed repetition frequencies.

The movement control unit 43 and the scanning control unit 45 respectively control the stage 3 and the galvanometer mirror 19 to perform scanning with measurement light and stimulus light on the DUT 10. At this time, the movement control unit 43 performs control so that scanning is performed with measurement light and stimulus light while concentration estimation processing (which will be described below) is performed targeting each of the places in the DUT 10.

The concentration estimation unit 47 executes the concentration estimation processing for estimating the concentration of impurities or the like targeting each of the places in the DUT 10 on the basis of information of the phase delay for each of the frequencies of the detection signals output from the network analyzer 35 (details of the concentration estimation processing will be described below). The output unit 49 generates an output image showing a distribution of the concentrations of impurities or the like by mapping the values of the concentrations for the respective places in the DUT 10 estimated by the concentration estimation unit 47 on an image and outputs the generated image to the input/output device of the output image.

Figure 3:
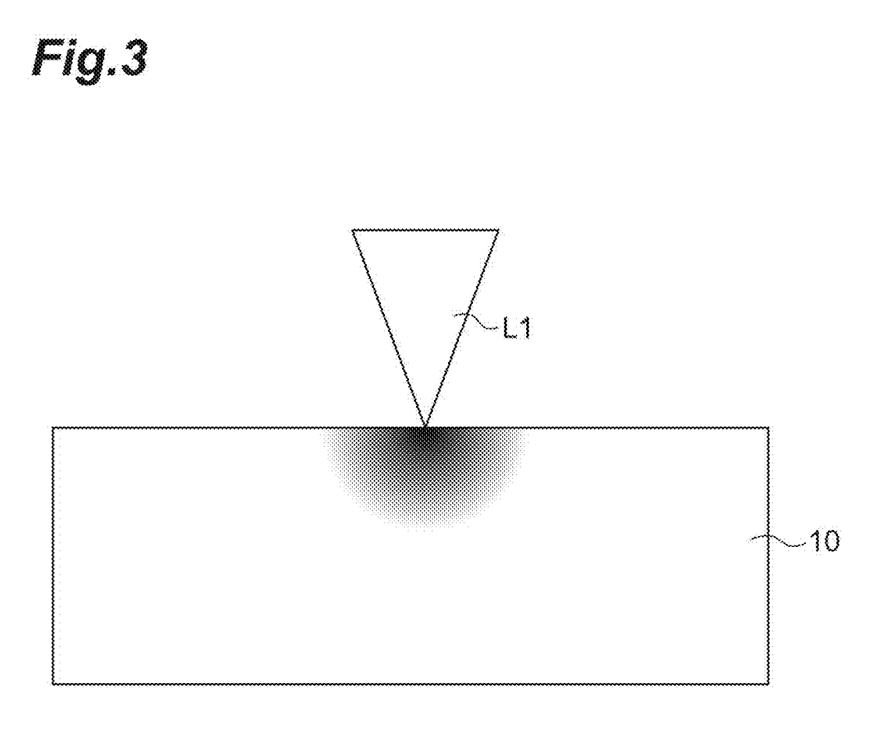
FIG. 3 is a view of an irradiation state of measurement light and stimulus light in a DUT 10 viewed in a direction perpendicular to optical axes of the measurement light and the stimulus light.
Figure 4:
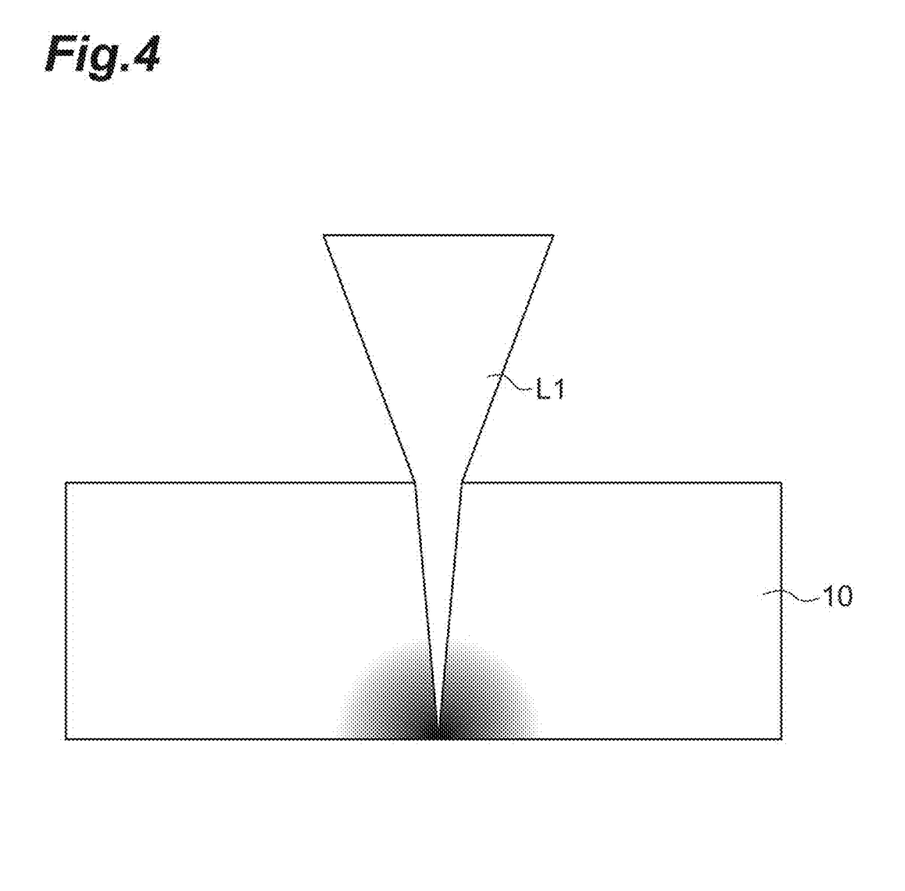
FIG. 4 is a view of another irradiation state of measurement light and stimulus light in the DUT 10 viewed in a direction perpendicular to the optical axes of the measurement light and the stimulus light.

A phenomenon measured by the concentration measurement device 1 having the foregoing configuration will be described. FIGS. 3 and 4 are views of irradiation states of measurement light and stimulus light in the DUT 10 viewed in a direction perpendicular to optical axes of the measurement light and the stimulus light.

Due to the light irradiation/light guiding system 5, the DUT 10 is irradiated with stimulus light, which includes a wavelength associated with an energy higher than a band-gap energy, while the stimulus light is subjected to intensity modulation. At the same time, irradiation is performed with measurement light having a different wavelength at a uniform intensity. At this time, carriers are generated inside the DUT 10 due to the stimulus light, and these carriers become extinct due to recombination at a speed depending on the concentration of impurities and the concentration of defects inside the DUT 10 at a timing when the intensity of the stimulus light is weakened.

A refraction index and a transmission factor inside the DUT 10 are influenced by the carrier density inside the substrate of the DUT 10. Due to this influence, the measurement light is modulated depending on the modulation state of the stimulus light when the measurement light is reflected on the front surface of the substrate or the rear surface of the substrate. The state of modulation of measurement light varies in accordance with the recombination speed of carriers. That is, recombination occurs at a high speed in a region in which the concentration inside the substrate is high, and recombination occurs at a low speed in a region in which the concentration is low. As a result, regarding reflected light generated due to reflection of measurement light, the amplitude increases when recombination occurs at a high speed. On the other hand, the amplitude decreases when recombination occurs at a low speed and the phase is delayed with respect to stimulus light at the same time.

FIG. 3 shows a state in which the front surface of the substrate of the DUT 10 on the light irradiation/light guiding system 5 side is set to be irradiated with synthetic light L1 of measurement light and stimulus light. In this case, the stimulus light generates plenty of electron-positive hole pairs in the vicinity of the front surface of the substrate. When the DUT 10 is a semiconductor substrate, the DUT 10 has a concentration of impurities to a certain degree. Therefore, a majority carriers (electrons in a case of an n-type substrate and positive holes in a case of a p-type substrate) are present in a uniform quantity in accordance with this concentration of impurities, and a minority carriers (positive holes in a case of an n-type substrate and electrons in a case of a p-type substrate) are also present. When stimulus light is incident in this state, the refraction index of the substrate changes due to the carriers, which are present excessively in the incidence region. It is known that a reflection factor R between atmospheric air and a substrate is expressed by the following expression $R=((n-1)/(n+1))^2$ when the refraction index of atmospheric air is "1" and the refraction index of the substrate is n. The reflection factor R also changes as the refraction index n changes due to generation and extinction of carriers, and thus reflected light is modulated.

Meanwhile, FIG. 4 shows a state in which the rear surface of the substrate of the DUT 10 on a side opposite to the light irradiation/light guiding system 5 is set to be irradiated with the synthetic light L1 of measurement light and stimulus light in a manner of being transmitted therethrough. In this case, reflected light also receives the influence of carriers in an optical path in addition to the influence of carriers on the reflection surface in the case of the FIG. 3. Specifically, an effect of attenuation of light occurs in addition to a change in refraction index due to the carriers in the optical path, and therefore the reflected light is influenced by both. An excessively minority carriers become extinct at a speed proportional to the product of the density of a majority carriers, that is, the concentration of impurities in the substrate and the density of an excessively minority carriers (more strictly speaking, an excessively minority carriers is reduced at a speed proportional to the difference with respect to the product of the excess part and a majority carriers). As a result, when stimulus light decreases, the refraction index returns to the original state at a speed proportional to the concentration of impurities in the substrate. However, this change in refraction index is considerably smaller than the extent of the refraction index of the substrate itself.

When the reflected light in the case shown in FIG. 3 or 4 is observed, the intensity of the reflected light changes substantially in association with a change in refraction index, and a time constant of a change in reflected light with respect to a change in stimulus light is inversely proportional to the concentration of impurities in the substrate.

Figure 5:
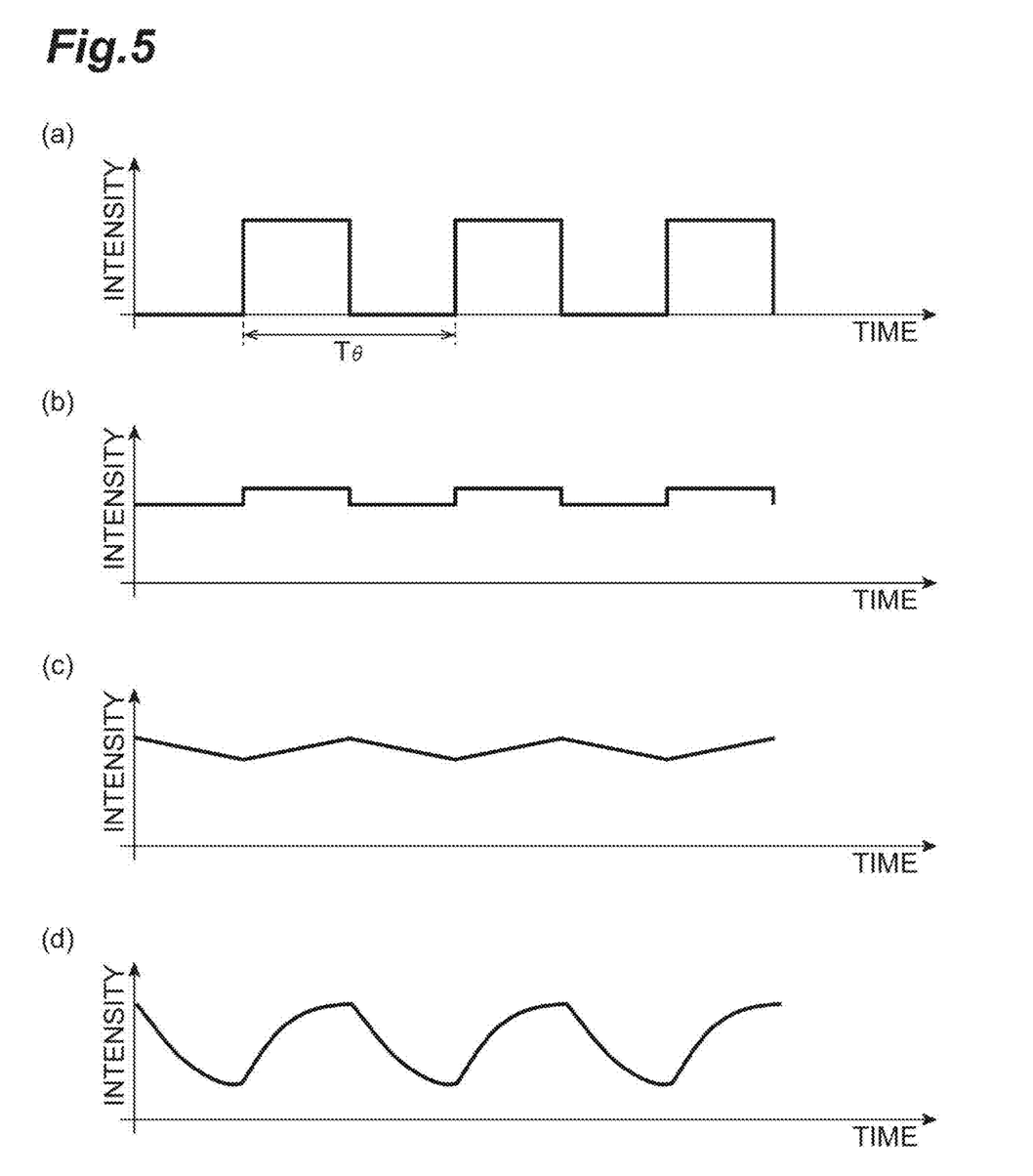
FIG. 5 is a view showing waveforms of changes in stimulus light and detection signal over time generated by the concentration measurement device 1.

In FIG. 5, the part (a) shows a waveform of a change in stimulus light used for irradiation of the concentration measurement device 1 over time, and the parts (b) to (d) show waveforms of changes in detection signal detected by the concentration measurement device 1 over time with respect to stimulus light having the waveform shown in the part (a). When a repetition cycle $T_0$ of the stimulus light is considerably larger than the time constant of a change in reflected light (the repetition frequency is low), the sensitivity of the phase delay observed in the detection signal becomes low as shown in the part (b). When the time constant of a change in reflected light is approximately half the repetition cycle $T_0$ of the stimulus light (when the time constant is comparatively large and the phase delay is approximately 90 degrees), a phase delay appears in a change in amplitude of the detection signal as shown in the part (c). A phase delay appears most notably in a change in amplitude of the detection signal, when the time constant of a change in reflected light is approximately ¼ (when the phase delay is 45 degrees) of the repetition cycle $T_0$ of the stimulus light as shown in the part (d).

In the present embodiment, the concentration of impurities or the like inside the DUT 10 is estimated by identifying the frequency of a detection signal causing a predetermined phase delay in accordance with the concentration thereof. Here, since rectangular waves also include not only a component of the repetition frequency but also a frequency component having higher harmonic waves thereof, the concentration can be estimated efficiently. Moreover, even when the concentration inside the DUT 10 is uncertain, the concentration thereof can be estimated by repetitively changing the repetition frequency and detecting the detection signal.

Hereinafter, details of a concentration measurement procedure including the concentration estimation processing in the concentration measurement device 1 will be described.

First, the DUT 10 is placed on the stage 3. When the DUT 10 is a bare wafer; a substrate subjected to epitaxial growth; a wafer substrate on which a well, a diffusion region, or the like is formed; or the like, the DUT 10 is placed so that it can be irradiated with measurement light and stimulus light from the front surface side of the substrate. When the DUT 10 is a semiconductor substrate on which a circuit element is formed, the DUT 10 is placed so that it can be irradiated with measurement light and stimulus light from the rear surface side of the substrate. When the DUT 10 is irradiated from the rear surface side, the rear surface may be polished as necessary, and a solid immersion lens may be used.

Thereafter, the DUT 10 is irradiated with measurement light and stimulus light from the light irradiation/light guiding system 5. At this time, the optical axes and the focal depths of the measurement light and the stimulus light are set in advance so that they become the same, and the light irradiation/light guiding system 5 is configured to be an optical system having a sufficiently small chromatic aberration. At this time, the front surface or the rear surface of the DUT 10 is subjected to angular adjustment to be perpendicular to the optical axes of the measurement light and the stimulus light, and the focal points of the measurement light and the stimulus light are also set to be focused on a measurement surface of the DUT 10.

Moreover, due to control of the controller 37, control is performed so that stimulus light is subjected to intensity modulation due to rectangular waves. The repetition frequency of these rectangular waves is set in advance in accordance with a postulated concentration of impurities and is set to approximately 1 kHz if the concentration of impurities is on the order of $10^{15}/cm^3$. The repetition frequency is set in a manner of being proportional to the postulated concentration with respect to the concentrations of impurities having other values.

Next, in the photo detector 29 of the control system 7, reflected light from the measurement surface of the DUT 10 is detected, a detection signal is generated, and the detection signal is amplified by the amplifier 31. Further, the component of the repetition frequency and the component of the higher harmonic waves thereof are extracted from the detection signal by the network analyzer 35 of the control system 7. At this time, a band width is set to avoid ground noise of 0 Hz.

In addition, in the network analyzer 35 of the control system 7, a phase delay with respect to the modulation signal of stimulus light is detected targeting the waveforms of the extracted detection signals having a plurality of frequencies. Moreover, association data in which information of each of the frequencies of the extracted detection signals and information of a detected phase delay targeting the detection signal are associated with each other is output to the controller 37 from the network analyzer 35.

Detection of the phase delay of the detection signals having the foregoing plurality of frequencies and outputting the association data related thereto may be performed repetitively targeting the plurality of repetition frequencies which have been repetitively set. Consequently, the concentration can be estimated even when the concentration of impurities or the like is uncertain. In addition, detection of the phase delay of the detection signals having the foregoing plurality of frequencies and outputting the association data related thereto are performed repetitively while measurement points on the DUT 10 are scanned due to control of the controller 37.

Thereafter, the concentrations of impurities or the like at a plurality of measurement points are estimated by the controller 37 using the association data related to the plurality of measurement points on the DUT 10 (concentration estimation processing). That is, a frequency at which the phase delay has a predetermined value is estimated, and the concentrations of impurities or the like at the measurement points on the DUT 10 are estimated on the basis of the frequency. At this time, when a frequency having a predetermined phase delay cannot be estimated, processing of detecting reflected light may be performed repetitively by further changing the repetition frequency.

More specifically, a frequency at which the phase delay becomes 45 degrees is estimated on the basis of the value of the phase delay of the detection signals having a plurality of frequencies. The frequency is referred to as a cutoff frequency, and a time constant τ at this time becomes $1/(2\pi)$ times of a cycle associated with the frequency. This time constant τ corresponds to a lifetime of carriers inside the DUT 10. Generally, the lifetime τ of carriers is expressed by the following expression $\tau=1/\{B(n_0+p_0+\Delta n)\}$ to $1/(B \cdot p_0)$ when B is the proportional constant, $p_0$ is the concentration of majority carriers (=concentration of impurities), $n_0$ is the concentration of minority carriers, and $\Delta n$ is the concentration of excess carriers. The controller 37 calculates the lifetime τ of carriers from the frequency at which the phase delay becomes 45 degrees utilizing the properties and calculates the concentration of impurities ($=p_0$) from the lifetime τ of carriers as an estimation value by inversely calculating the foregoing expression.

Figure 6:
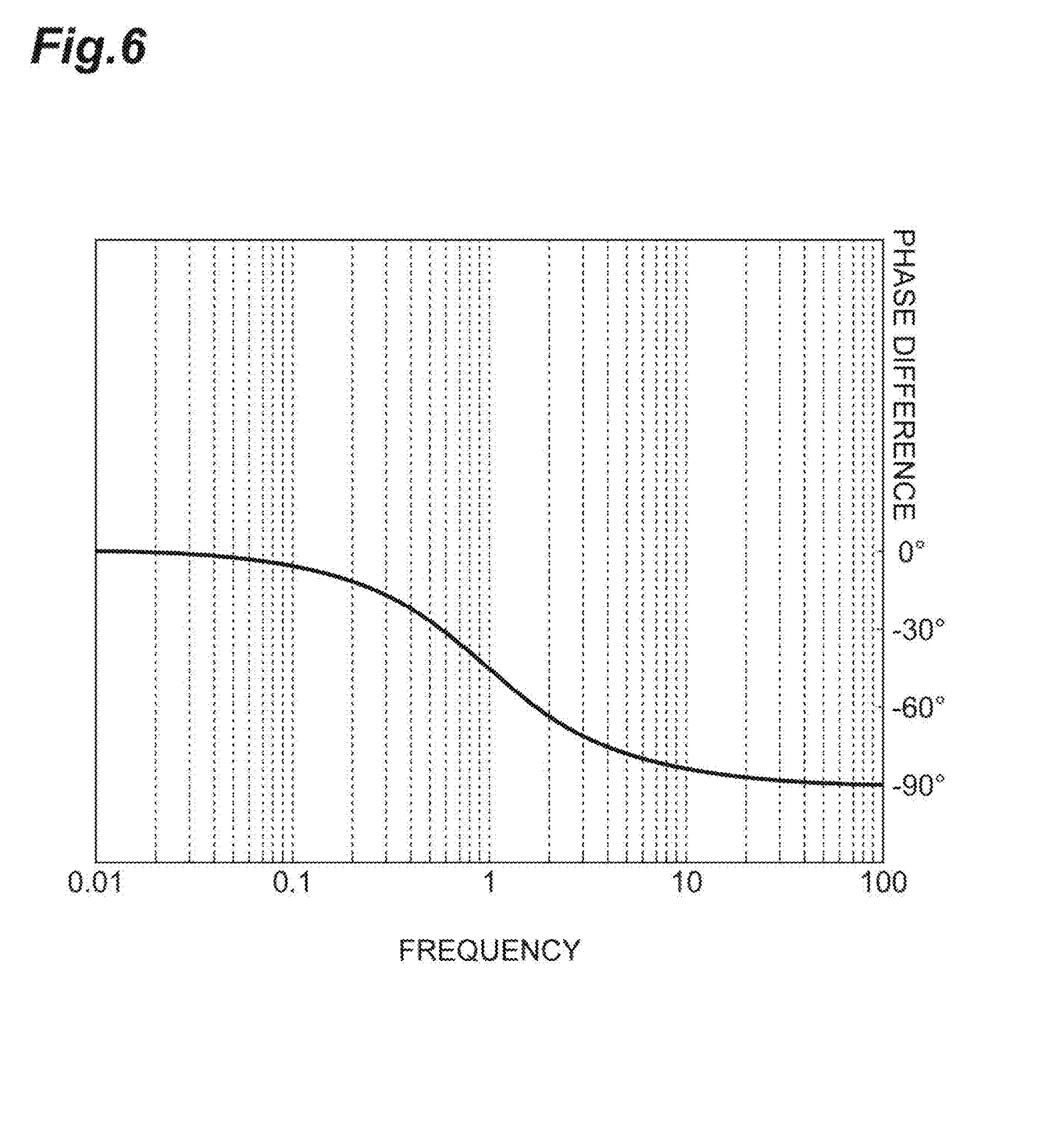
FIG. 6 is a graph showing an example of a correspondence relationship between a frequency and a phase delay, indicated by data stored in the controller 37 in FIG. 1 in advance.

Here, when a frequency at which the phase delay becomes 45 degrees is estimated on the basis of the value of the phase delay of the detection signals having a plurality of frequencies, a detection signal of which the phase delay coincides with 45 degrees is not necessarily extracted, and a frequency having a phase delay of 45 degrees may be obtained through analytical calculation such as curve fitting on the basis of generated association data. In this case, data indicating a correspondence relationship between the frequency and the phase delay is stored in advance in the controller 37, and a frequency at which the phase delay becomes 45 degrees is estimated by fitting a combination of the frequency of a detection signal and an actual measurement value of the phase delay in the correspondence relationship which has been stored in advance. FIG. 6 shows an example of a correspondence relationship between the frequency and the phase delay expressed by data stored in the controller 37 in advance (frequencies on the horizontal axis are frequencies in units of cutoff frequencies).

Lastly, values of the concentrations estimated regarding a plurality of measurement points are mapped on an image by the controller 37, and data of an output image indicating the concentration distribution on the DUT 10 is generated. Further, the output image is output to the input/output device on the basis of the data. With this output image, a fine concentration distribution on the DUT 10 can be observed within a high-dynamic range in a non-contact manner. For example, unevenness of the concentration of impurities can be easily observed. In addition, unevenness of heat dissipation characteristics on the DUT 10 can be measured at the same time.

According to the concentration measurement device 1 described above and a concentration measurement method using the concentration measurement device 1, the DUT 10 is irradiated with measurement light and stimulus light subjected to intensity modulation due to a modulation signal including a default frequency at the same time, and the intensity of reflected light from the DUT 10 is detected. As a result, the concentration of impurities in the DUT 10 is estimated on the basis of the output detection signal. At this time, a frequency at which the phase delay has a predetermined value is estimated on the basis of the phase delay of the detection signal with respect to the modulation signal, and the concentration of impurities is estimated on the basis thereof. Therefore, even when the concentration of impurities is unknown, it is possible to accurately measure the concentration of impurities associated with the lifetime of carriers.

In addition, in the present embodiment, a plurality of phase delays in a plurality of default frequencies are detected, and a frequency at which the phase delay has a predetermined value is estimated on the basis of the plurality of phase delays for the plurality of respective default frequencies. In this case, even when the concentration of impurities is unknown, it is possible to set a frequency of stimulus light causing a phase delay having a predetermined value associated therewith. As a result, even when the concentration of impurities is unknown, it is possible to accurately measure the concentration of impurities.

In addition, in the present embodiment, a frequency at which the phase delay of a detection signal becomes 45 degrees is estimated. In this manner, it is possible to more accurately measure the concentration of impurities on the basis of the cutoff frequency.

Moreover, in the present embodiment, irradiation is performed with stimulus light subjected to intensity modulation using the modulation signal for each of a plurality of default frequencies, and a detection signal is generated in association with each ray of the stimulus light. In this manner, even when the concentration of impurities changes extensively, it is possible to set a frequency of stimulus light causing a phase delay having a predetermined value associated therewith. As a result, even when the concentration of impurities changes extensively, it is possible to accurately measure the concentration of impurities.

In addition, in the present embodiment, stimulus light subjected to intensity modulation due to rectangular waves is used. According to such a configuration, the phase delay of the detection signals having a plurality of frequencies can be easily acquired. As a result, it is possible to efficiently set a frequency of stimulus light causing a phase delay having a predetermined value associated with a concentration of impurities. Therefore, even when the concentration of impurities is unknown, it is possible to efficiently measure the concentration of impurities.

Moreover, in the present embodiment, stimulus light having an energy higher than the band-gap energy of a semiconductor configuring the DUT 10 is used. According to such a configuration, carriers can be generated efficiently in the DUT 10, and the concentration of impurities can be measured more accurately.

Hereinabove, various embodiments of the present invention have been described. However, the present invention is not limited to the foregoing embodiments and may be modified or may be applied to other configurations within a range not changing the gist described in each of the claims.

Regarding the DUT 10 serving as a measurement target object in the foregoing embodiment, a semiconductor substrate in which impurities are diffused in a process of manufacturing a semiconductor device such as an LSI may be selected. When measurement of a concentration is executed targeting such a semiconductor substrate, measurement points which are measurement target places of the DUT 10 are set in advance by the controller 37, and the light irradiation/light guiding system 5 is controlled so that the measurement points are scanned. In addition, information of a postulated concentration of impurities is input to the controller 37 in advance via the input/output device. Further, the controller 37 compares the numerical value of the concentration of impurities estimated regarding the measurement points and information of the concentration of impurities input in advance to each other and outputs the comparison result (for example, a result of determining whether or not they coincide with each other within a range of a predetermined error) to the input/output device. In such a configuration, it is possible to determine whether or not a diffusion region is suitably generated in the process of manufacturing a semiconductor device.

The light irradiation/light guiding system 5 of the foregoing embodiment is configured to be able to guide reflected light from the DUT 10 toward the control system 7 but may be configured to be able to guide transmitted light generated when measurement light is transmitted through the DUT 10 toward the control system 7. In this case, the concentration is estimated on the basis of the detection signal generated by detecting transmitted light in the control system 7.

The light irradiation/light guiding system 5 of the foregoing embodiment may include a fiber coupler as an element for synthesizing measurement light and stimulus light in place of the dichroic mirror 13 or may include fibers having a plurality of cores.

In the light irradiation/light guiding system 5 of the foregoing embodiment, the polarization beam splitter 15 may be disposed between the dichroic mirror 13 and the light source 9a. In this case, the dichroic mirror 13 plays a role of the optical filter 25.

The light irradiation/light guiding system 5 of the foregoing embodiment is configured so that the optical axes and the focal points coincide with each other between measurement light and stimulus light. However, if spots of stimulus light at the measurement points in the DUT 10 include spots of measurement light, the focal points do not necessarily coincide with each other. In addition, when fibers having a plurality of cores are used, the optical axes may be set in a misaligned manner between measurement light and stimulus light.

In addition, in the foregoing embodiment, if the photo detector 29 is configured to be sensitive to only measurement light, the optical filter 25 may be omitted.

In addition, in the foregoing embodiment, measurement is performed using stimulus light subjected to intensity modulation due to rectangular waves. However, a plurality of rays of stimulus light which are subjected to intensity modulation using a signal having a different waveform such as sine waves and which are associated with a plurality of respective frequencies may be used.

In the foregoing embodiment, it is favorable that in an estimation step, a plurality of phase delays in a plurality of default frequencies be detected, and a frequency at which the phase delay has a predetermined value be obtained on the basis of the plurality of phase delays for the plurality of respective default frequencies. In another embodiment described above, it is favorable that the analysis unit detect a plurality of phase delays in a plurality of default frequencies and obtain a frequency at which the phase delay has a predetermined value on the basis of the plurality of phase delays for the plurality of respective default frequencies. In this case, even when the concentration of impurities is unknown, it is possible to set a frequency of stimulus light causing a phase delay having a predetermined value associated therewith. As a result, even when the concentration of impurities is unknown, it is possible to accurately measure the concentration of impurities.

In addition, it is also favorable that in an irradiation step, irradiation be performed with stimulus light subjected to intensity modulation due to the modulation signal having rectangular waves. It is also favorable that the modulation unit perform intensity modulation of stimulus light using the modulation signal having rectangular waves. According to the configuration, it is possible to efficiently set a frequency of stimulus light causing a phase delay having a predetermined value associated with a concentration of impurities. As a result, even when the concentration of impurities is unknown, it is possible to efficiently measure the concentration of impurities.

Moreover, it is also favorable that in the irradiation step, irradiation be performed with stimulus light subjected to intensity modulation using the modulation signal for each of a plurality of the default frequencies, and in an outputting step, the detection signal be output in association with each ray of the stimulus light. It is also favorable that the modulation unit perform intensity modulation of the stimulus light using the modulation signal for each of a plurality of the default frequencies, and the photo detector output the detection signal in association with each ray of the stimulus light. In this case, even when the concentration of impurities changes extensively, it is possible to set a frequency of stimulus light causing a phase delay having a predetermined value associated therewith. As a result, even when the concentration of impurities changes extensively, it is possible to accurately measure the concentration of impurities.

In addition, it is also favorable that a frequency at which the phase delay of a detection signal becomes 45 degrees be estimated. In this case, it is possible to more accurately measure the concentration of impurities by identifying the cutoff frequency.

Further in addition, it is also favorable that in the irradiation step, irradiation be performed with stimulus light having an energy higher than a band-gap energy of the semiconductor configuring the measurement target object. It is also favorable that the second light source generate stimulus light having an energy higher than the band-gap energy of the semiconductor configuring the measurement target object. According to the configuration, it is possible to efficiently generate carriers in a measurement target object due to irradiation of stimulus light, and it is possible to more accurately measure the concentration of impurities.

In addition, it is also favorable that the foregoing embodiment further include a comparing step of comparing information of a concentration of impurities input in advance and the concentration of impurities estimated in the estimation step. It is also favorable that the analysis unit compare information of a concentration of impurities input in advance and the estimated concentration of impurities to each other. When such a configuration is employed, it is possible to determine whether or not a concentration of impurities in a measurement target object is a desired concentration. For example, it is possible to realize monitoring during a manufacturing process.

Moreover, it is also favorable that in the estimation step image data indicating a distribution of a concentration of impurities be generated by mapping the estimated concentration of impurities. It is also favorable that the analysis unit generate image data indicating a distribution of a concentration of impurities by mapping the estimated concentration of impurities. In this case, it is possible to easily measure the distribution of the concentration of impurities in a measurement target object, and it is possible to easily analyze a measurement target object such as a semiconductor substrate.

INDUSTRIAL APPLICABILITY

An embodiment is used for a concentration measurement method and a concentration measurement device for measuring a concentration of impurities in a measurement target object, and it is possible to accurately measure a concentration of impurities in a measurement target object.

REFERENCE SIGNS LIST

1 Concentration measurement device
5 Light irradiation/light guiding system (optical system)
7 Control system
9a Light source (first light source)
9b Light source (second light source)
29 Photo detector
33 Modulation signal source (modulation unit)
35 Network analyzer (analysis unit)
37 Controller (analysis unit)

The invention claimed is:

1. A concentration measurement method for measuring a concentration of impurities in a measurement target object, the concentration measurement method comprising:
   irradiating the measurement target object with measurement light and stimulus light subjected to intensity modulation using a modulation signal including a default frequency;
   outputting a detection signal by detecting an intensity of reflected light from the measurement target object or transmitted light through the measurement target object; and
   detecting a phase delay of the detection signal with respect to the modulation signal, obtaining a frequency at which the phase delay has a predetermined value, and estimating a concentration of impurities in the measurement target object on the basis of a time constant corresponding to a lifetime of carriers in the measurement target object, calculated from the obtained frequency.

2. The concentration measurement method according to claim 1, wherein the detection signal is one of a plurality of detection signals outputted by detecting an intensity of reflected light from the measurement target object or transmitted light through the measurement target object, further comprising:
   detecting, for each of the detection signals, a phase delay of the detection signal with respect to the modulation signal;
   obtaining, for each of the detected phase delays, a frequency at which the phase delay has a predetermined value; and
   estimating the concentration of impurities in the measurement target object on the basis of a time constant corresponding to a lifetime of carriers in the measurement target object, calculated from the obtained frequencies.

3. The concentration measurement method according to claim 1,
   wherein irradiation is performed with the stimulus light subjected to intensity modulation due to the modulation signal having rectangular waves.

4. The concentration measurement method according to claim 2,
   wherein irradiation is performed with the stimulus light subjected to intensity modulation using the modulation signal for each of the obtained frequencies, and wherein each of the detection signals is output in association with each ray of the stimulus light.

5. The concentration measurement method according to claim 1,
   wherein the predetermined value is 45 degrees.

6. The concentration measurement method according to claim 1,
   wherein irradiation is performed with stimulus light having an energy higher than a band-gap energy of a semiconductor configuring the measurement target object.

7. The concentration measurement method according to claim 1, further comprising:
   comparing information of a concentration of impurities input in advance and the concentration of impurities estimated to each other.

8. The concentration measurement method according to claim 1,
   wherein image data indicating a distribution of a concentration of impurities is generated by mapping the estimated concentration of impurities.

9. A concentration measurement device for measuring a concentration of impurities in a measurement target object, the concentration measurement device comprising:
   a first light source configured to generate measurement light;
   a second light source configured to generate stimulus light;
   a modulator configured to perform intensity modulation of the stimulus light using a modulation signal including a default frequency;
   a photo detector configured to output a detection signal by detecting an intensity of reflected light from the measurement target object or transmitted light through the measurement target object;
   an optical system configured to guide the measurement light and the stimulus light subjected to intensity modulation toward the measurement target object and to guide reflected light from the measurement target object or transmitted light through the measurement target object toward the photo detector; and
   an analyzer configured to detect a phase delay of the detection signal with respect to the modulation signal, to obtain a frequency at which the phase delay has a predetermined value, and to estimate a concentration of impurities in the measurement target object on the basis of a time constant corresponding to a lifetime of carriers in the measurement target object, calculated from the obtained frequency.

10. The concentration measurement device according to claim 9,
    wherein the analyzer is configured to detect a plurality of phase delays of a plurality of detection signals having default frequencies and to obtain, for each of the detected phase delays, a frequency at which the phase delay has a predetermined value.

11. The concentration measurement device according to claim 9,
    wherein the modulator performs intensity modulation of the stimulus light using the modulation signal having rectangular waves.

12. The concentration measurement device according to claim 10,
    wherein the modulator performs intensity modulation of the stimulus light using the modulation signal for each of the default frequencies, and wherein the photo detector outputs each of the detection signals in association with each ray of the stimulus light.

13. The concentration measurement device according to claim 9,
wherein the predetermined value is 45 degrees.

14. The concentration measurement device according to claim 9,
wherein the second light source generates stimulus light having an energy higher than a band-gap energy of a semiconductor configuring the measurement target object.

15. The concentration measurement device according to claim 9,
wherein the analyzer compares information of a concentration of impurities input in advance and the estimated concentration of impurities to each other.

16. The concentration measurement device according to claim 9,
wherein the analyzer generates image data indicating a distribution of a concentration of impurities by mapping the estimated concentration of impurities.

* * * * *